United States Patent [19]

Saville

[11] Patent Number: Plant 5,415

[45] Date of Patent: Mar. 12, 1985

[54] ROSE PLANT

[75] Inventor: F. Harmon Saville, Rowley, Mass.

[73] Assignee: Nor'East Miniature Roses, Inc., Rowley, Mass.

[21] Appl. No.: 556,269

[22] Filed: Nov. 30, 1983

[51] Int. Cl.[3] ..... A01H 5/00

[52] U.S. Cl. ..... Plt./10

[58] Field of Search ..... Plt./10

*Primary Examiner*—Robert E. Bagwill
*Attorney, Agent, or Firm*—Vincent G. Gioia

[57] ABSTRACT

A new miniature rose variety of bright orange red coloring of good exhibition form and good substance.

1 Drawing Figure

The present invention relates to a new and distinct variety of rose plant of the miniature rose class, which was originated by my crossing as seed parent the rose known as "Zorina" (U.S. Plant Pat. No. 2,321) and the rose known as "Poker Chip" (U.S. Plant Pat. No. 4,582) as pollen parent. The varietal denomination of this new variety is "Savaweek".

Among the novel characteristics possessed by this new variety which distinguish it from its parent and all other varieties of which I am aware are its bright orange red flowers of good exhibition form and thick petals which open well in varied weather conditions. Asexual reproduction by budding of the new variety as performed in Essex County, Massachusetts, shows that the foregoing and other distinguishing characteristics come true to form and are established and transmitted through succeeding propagations.

The accompanying drawings show typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "34A" is plate 34A of The Royal Horticultural Society Colour Chart.

Parentage: Seedling.
*Seed parent.*—"Zorina".
*Pollen parent.*—"Poker Chip".
Class: Miniature.

The following observations are made of specimens grown outdoors in Essex County, Massachusetts during the month of October.

FLOWER

Blooming habit: Recurrent.
Bud:
(1) *Size.*—Medium.
(2) *Form.*—Long pointed.
(3) *Color.*—When sepals first divide — near 34A.
(4) *Sepals.*—Longer than bud, lightly foliated.
(5) *Peduncle.*—Length — 1 to $1\frac{1}{4}$ inches. Aspect — straight. Strength — erect. Color — near 145A.

Bloom:
(1) *Size.*—Average size when fully expanded — about $1\frac{1}{4}$ to $1\frac{1}{2}$ inches.

(2) *Borne.*—Singly and small sprays.
(3) *Form.*—High centered at first, becoming flat, some petals reflex to quills upon opening; others roll under; flower maintains symmetrical exhibition form until center is lost. Flower opens well under variable weather conditions.
(4) *Petalage.*—Number of petals under normal conditions — about 15 to 18.
(5) *Color.*—As orange red buds 34A unfurl color remains stable between 34A and 34B with petal underside surface slightly lighter. Color holds upon aging. Color at point of petal attachment is near 6C.

Petals:
(1) *Texture.*—Thick, good substance.
(2) *Appearance.*—Inside — satiny, outside — satiny.
(3) *Form.*—Rounded, fan shaped.
(4) *Arrangement.*—Regularly arranged, shingle-like.
(5) *Petaloids in center.*—Very few.
(6) *Persistence.*—Drop off cleanly.
(7) *Fragrance.*—Slight.
(8) *Lasting quality.*—Moderately long lasting on plant and as cut flower.

REPRODUCTIVE ORGANS

Stamens, filaments and anthers:
(1) *Arrangement.*—Regularly arranged around styles.
(2) *Color.*—Near 23B.

Pollen: Color — near 23A.
Styles: Even, medium length.
Stigmas: Color — near 4D.
Hips: Shape — globular. Size — about $\frac{3}{4}$ inch. Color — orange. Do seeds protrude? — No.

PLANT

Form: Upright
Growth: Vigorous, well branched. Height attained — about 12 to 16 inches.
Foliage: Compound 5 to 7 leaflets.
(1) *Size.*—Medium.
(2) *Quantity.*—Abundant.
(3) *Color.*—New foliage: Upper side — near to 143A. Under side — near to 138B. Old foliage: Upper side — near 136B. Under side — near 136B.
(4) *Shape.*—Oval, pointed.
(5) Texture.—Upper side is slightly glossy and under side is matte.

(6) *Edge.*—Serrated.

(7) *Serration.*—Serrate.

(8) *Leaf stem.*—Color — near to 187D. Under side — near 146D.

(9) *Stipules.*—Medium, slightly bearded.

(10) *Resistance to disease.*—Blackspot — average. Mildew — average. Rust — average.

Wood:

(1) *New wood.*—Color — near 138A. Bark — smooth.

(2) *Old wood.*—Color — near 138A. Bark — smooth.

Thorns:

(1) *Thorns.*—Quantity (main stalk): moderate. On laterals from stalk — moderate. Form — Long, straight, angled slightly downward. Length — medium. Color — near 185D. Position — irregular.

(2) *Prickles.*—None.

Winter hardiness: Requires ordinary protection in extreme climates.

I claim:

1. A new and distinct variety of rose plant of the miniature rose class, substantially as shown and described, characterized particularly by bright orange red flowers of good exhibition form and substance with petals reflexing and rolling under upon opening while retaining good form.

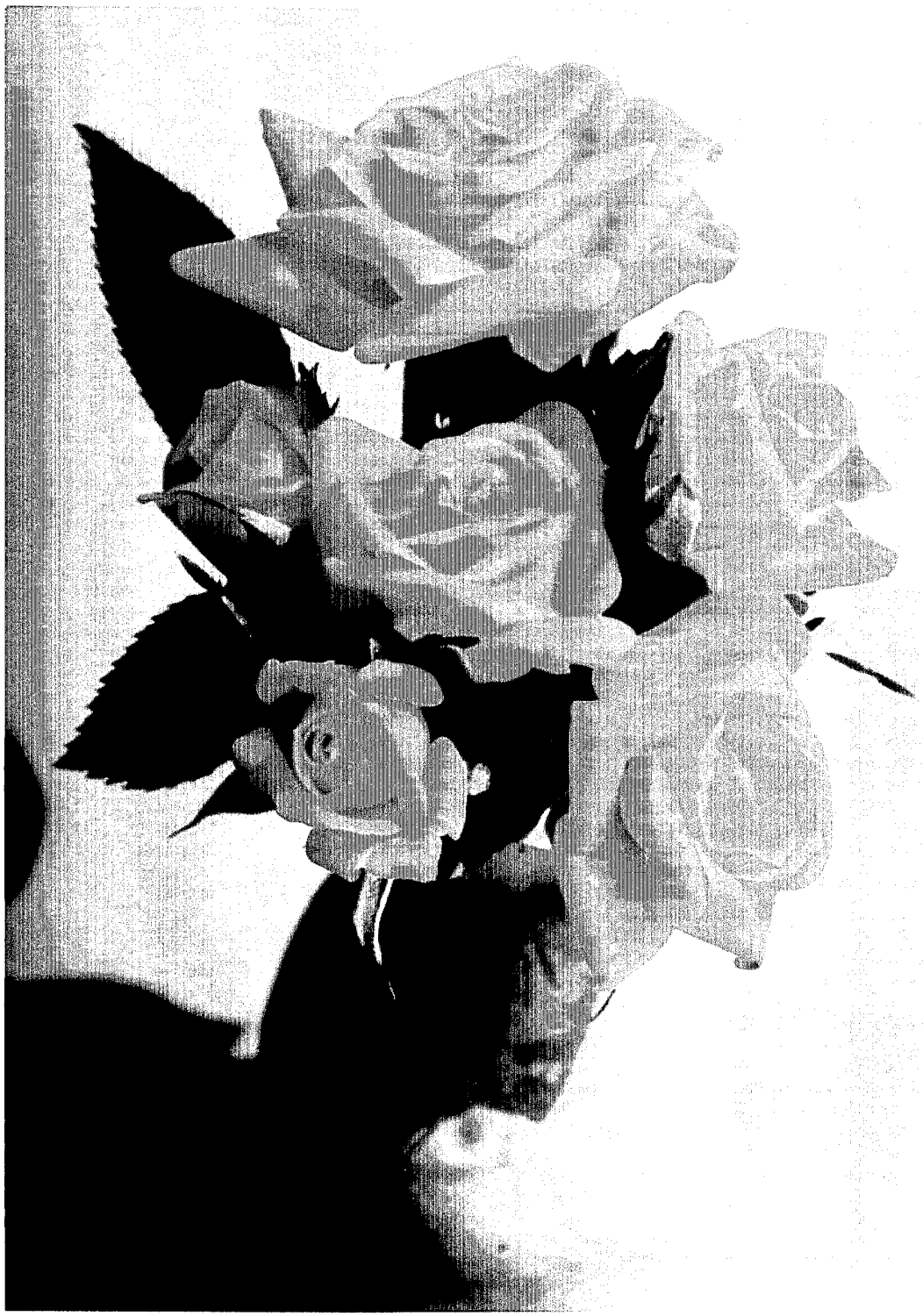

* * * * *